United States Patent
Schaefer et al.

(10) Patent No.: US 8,269,161 B2
(45) Date of Patent: Sep. 18, 2012

(54) APPARATUS AND METHOD FOR EVALUATING DOWNHOLE FLUIDS

(75) Inventors: Peter Schaefer, Grob Kreutz (DE); Tobias Kischkat, Niedersachsen (DE)

(73) Assignee: Baker Hughes Incorporated, Houston, TX (US)

( * ) Notice: Subject to any disclaimer, the term of this patent is extended or adjusted under 35 U.S.C. 154(b) by 415 days.

(21) Appl. No.: 12/333,525

(22) Filed: Dec. 12, 2008

(65) Prior Publication Data
US 2010/0148785 A1 Jun. 17, 2010

(51) Int. Cl.
*G01V 5/04* (2006.01)
(52) U.S. Cl. .................... 250/258; 250/256; 250/253
(58) Field of Classification Search .............. 250/258, 250/256, 253
See application file for complete search history.

(56) References Cited

U.S. PATENT DOCUMENTS

| | | | |
|---|---|---|---|
| 3,312,824 A | 4/1967 | Cook | |
| 3,503,685 A | 3/1970 | Driscoll et al. | |
| 3,566,111 A | 2/1971 | Harm | |
| 3,756,721 A | 9/1973 | Williams | |
| 4,612,440 A | 9/1986 | Brunnee et al. | |
| 5,451,780 A | 9/1995 | Laser | |
| 5,627,671 A | 5/1997 | Yamura et al. | |
| 5,661,589 A | 8/1997 | Meyer | |
| 5,866,430 A | 2/1999 | Grow | |
| 5,880,833 A | 3/1999 | Iwasaki | |
| 6,176,323 B1 | 1/2001 | Weirich et al. | |
| 6,388,251 B1 | 5/2002 | Papanyan | |
| 6,437,326 B1 | 8/2002 | Yamate et al. | |
| 6,678,050 B2 | 1/2004 | Pope et al. | |
| 6,765,707 B2 | 7/2004 | Ishikawa et al. | |
| 6,798,518 B2 | 9/2004 | Difoggio et al. | |
| 6,913,079 B2 * | 7/2005 | Tubel ................ 166/250.01 |
| 6,956,648 B2 * | 10/2005 | Loicht et al. .................. 356/323 |
| 7,167,239 B2 | 1/2007 | Yamamoto | |
| 7,265,827 B2 | 9/2007 | Slutter et al. | |
| 2002/0043620 A1 | 4/2002 | Tchakarov et al. | |
| 2003/0048450 A1 | 3/2003 | Pope et al. | |
| 2003/0223069 A1 | 12/2003 | DiFoggio et al. | |
| 2004/0007665 A1 | 1/2004 | DiFoggio et al. | |
| 2004/0045705 A1 | 3/2004 | Gardner et al. | |
| 2004/0061858 A1 | 4/2004 | Pope et al. | |
| 2005/0007583 A1 | 1/2005 | DiFoggio | |
| 2005/0099618 A1 | 5/2005 | DiFoggio et al. | |

(Continued)

FOREIGN PATENT DOCUMENTS

JP 60093924 5/1985

(Continued)

OTHER PUBLICATIONS

B.M. Freifeld, et al. "Real-time quadrupole mass spectrometer analysis of gas in borehole fluid samples acquired using the U-tube sampling methodology". Geofluids (2006) 6, 217-224.

(Continued)

*Primary Examiner* — Christine Sung
(74) *Attorney, Agent, or Firm* — Cantor Colburn LLP

(57) ABSTRACT

An apparatus for evaluating downhole fluids is disclosed. The apparatus includes: an optical block having an adjustable opening that receives electromagnetic energy emitted by an electromagnetic energy source; a controller operatively associated with the optical block for adjusting the opening size, wherein the opening size is adjusted at least in part based on one or more estimated downhole parameters; and a sensor that receives the electromagnetic energy emitted by the electromagnetic energy source after the emitted electromagnetic energy interacts with a downhole fluid. A method for evaluating downhole fluids is also disclosed.

29 Claims, 4 Drawing Sheets

U.S. PATENT DOCUMENTS

| | | |
|---|---|---|
| 2006/0142955 A1 | 6/2006 | Jones et al. |
| 2007/0013911 A1 | 1/2007 | DiFoggio |
| 2007/0035736 A1 | 2/2007 | Vannuffelen et al. |
| 2007/0109537 A1 | 5/2007 | Vannuffelen et al. |
| 2007/0159625 A1 | 7/2007 | DiFoggio |
| 2007/0171414 A1* | 7/2007 | Vannuffelen et al. ......... 356/328 |

FOREIGN PATENT DOCUMENTS

| | | |
|---|---|---|
| JP | 64086027 | 3/1989 |
| JP | 06012093 | 4/1994 |
| JP | 10111175 | 4/1998 |
| JP | 2005207982 | 4/2005 |

OTHER PUBLICATIONS

C.W. Morris, et al. "Using Optical Fluid Analysis to Evaluate Downhole Fluid Sample Contamination". SPE 50603. 1998 SPE European Petroleum Conference held in The Hague, The Netherlands, Oct. 20-22, 1998.

I. A. Shkrob, et al. "Frequency-domain "single-shot" (FDSS) transient absorption spectroscopy using a variable length grating pair compressor." Mar. 17, 2004, Chemistry Division Argonne National Laboratory.

* cited by examiner

APPARATUS AND METHOD FOR EVALUATING DOWNHOLE FLUIDS

BACKGROUND

1. Technical Field

The present disclosure generally relates to formation evaluation and in particular to methods and apparatus for evaluating downhole fluids.

2. Background Information

Information about the subterranean formations traversed by the borehole may be obtained by any number of techniques. Techniques used to obtain formation information include obtaining one or more core samples of the subterranean formations and obtaining fluid samples produced from the subterranean formations. These samplings are collectively referred to herein as formation sampling. Core samples are often retrieved from the borehole and tested in a rig-site or remote laboratory to determine properties of the core sample, which properties are used to estimate formation properties. Modern fluid sampling includes various downhole tests and sometimes fluid samples are retrieved for surface laboratory testing.

One useful tool for evaluating downhole fluids is the spectrometer, and it is sometimes desirable to place some or all of the spectrometer components downhole. Current downhole spectrometers suffer in that the downhole environmental conditions, for example the high temperature environment, adversely affect the spectrometer resolution.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

Disclosed is an apparatus for evaluating downhole fluids. The apparatus includes: an optical block having an adjustable opening that receives electromagnetic energy emitted by an electromagnetic energy source; a controller operatively associated with the optical block for adjusting the opening size, wherein the opening size is adjusted at least in part based on one or more estimated downhole parameters; and a sensor that receives the electromagnetic energy emitted by the electromagnetic energy source after the emitted electromagnetic energy interacts with a downhole fluid.

An exemplary method for evaluating downhole fluids includes: emitting electromagnetic energy toward an optical block having an adjustable opening; estimating one or more downhole parameters; adjusting the opening size at least in part based on the one or more estimated downhole parameters using a controller; and receiving with a sensor electromagnetic energy emitted by the electromagnetic energy source after the emitted electromagnetic energy interacts with a downhole fluid.

BRIEF DESCRIPTION OF THE DRAWINGS

For a detailed understanding of the present disclosure, reference should be made to the following detailed description of the several non-limiting embodiments, taken in conjunction with the accompanying drawings, in which like elements have been given like numerals and wherein.

DESCRIPTION OF EXEMPLARY EMBODIMENTS

Figure 1:
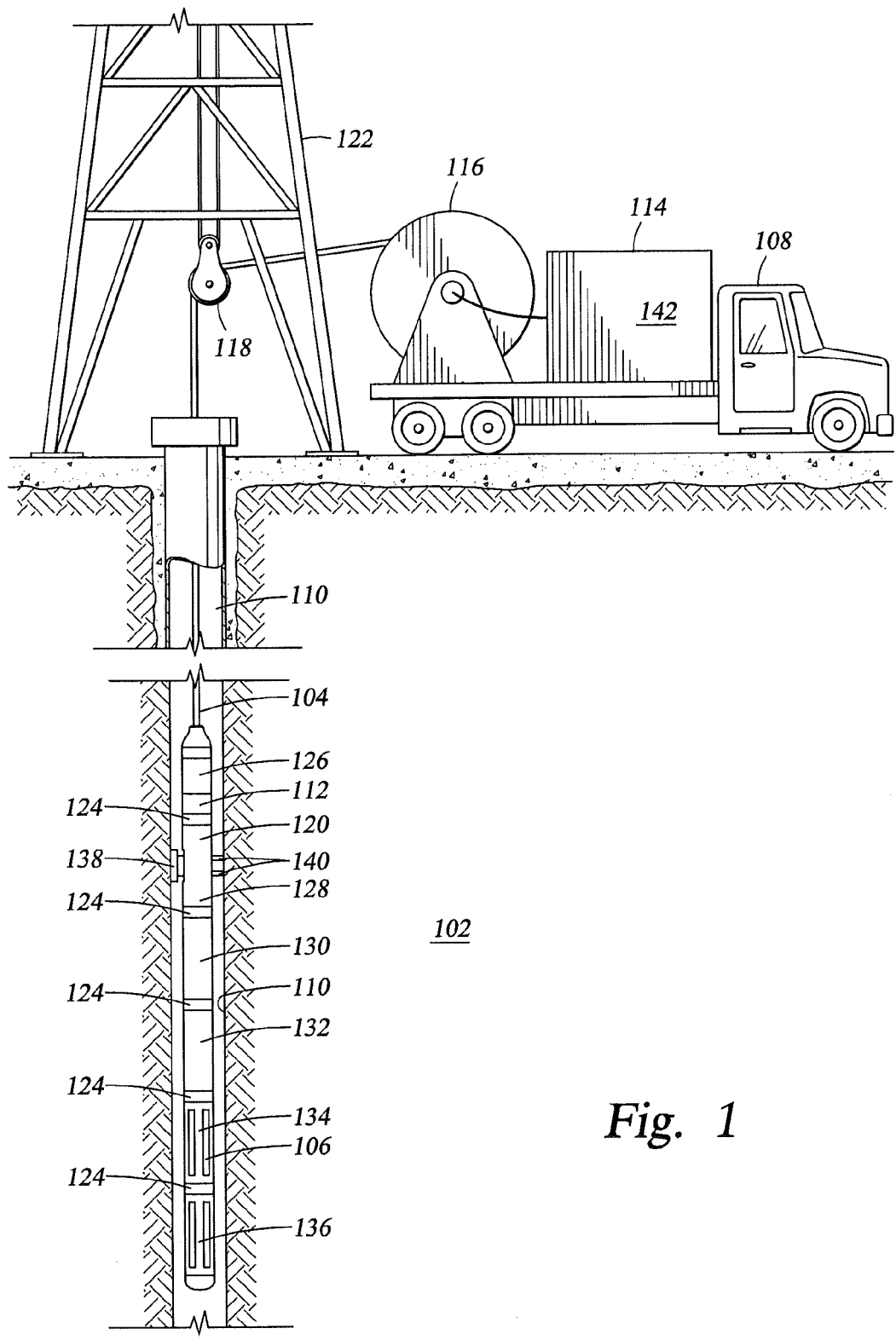
FIG. 1 is an exemplary wireline system according to several embodiments of the disclosure.

FIG. 1 schematically illustrates a non-limiting example of a wireline apparatus 100 according to several disclosed embodiments. In the example shown, a well borehole 110 traverses several subterranean formations 102. The well borehole 110 will typically be filled or at least partially filled with a fluid mixture which can include various gases, water, drilling fluid, and formation fluids that are indigenous to the subterranean formations penetrated by the well borehole. Such fluid mixtures are referred herein to as "well borehole fluids".

A formation evaluation tool 120 is conveyed in the well borehole 110 using a wire line 104. Wire line deployment and retrieval may be performed by a powered winch carried by a service truck 108, for example. The wireline 104 typically is an armored cable that carries data and power conductors for providing power to the formation evaluation tool 120 and to provide two-way data communication between a tool processor 112 and a controller 114 that may be carried by the service truck 108. The wireline 104 typically is carried from a spool 116 over a pulley 118 supported by a derrick 122. The spool 116 may be carried by the truck 108 as shown for on-land operations, by an offshore rig for underwater operations, or by any other suitable mobile or fixed supporting structure. The controller 114 may include a processor 142, such as within a computer or a microprocessor, data storage devices, such as solid state memory and magnetic tapes, peripherals, such as data input devices and display devices, and other circuitry for controlling and processing data received from the tool 120. The surface controller 114 may further include one or more computer programs embedded in a computer-readable medium accessible to the processor 142 in the controller 114 for executing instructions contained in the computer programs to perform the various methods and functions associated with the processing of the data from the tool 120.

The exemplary wireline FIG. 1 operates as a carrier for the formation evaluation tool 120, but any carrier is considered within the scope of the disclosure. The term "carrier" as used herein means any device, device component, combination of devices, media and/or member that may be used to convey, house, support or otherwise facilitate the use of another device, device component, combination of devices, media and/or member. Exemplary non-limiting carriers include drill strings of the coiled tube type, of the jointed pipe type and any combination or portion thereof. Other carrier examples include casing pipes, wirelines, wireline sondes, slickline sondes, drop shots, downhole subs, BHA's, drill string inserts, modules, internal housings and substrate portions thereof.

The lower portion of the formation evaluation tool 120 may include an assembly of several tool segments that are joined end-to-end by threaded sleeves or mutual compression unions 124. An assembly of tool segments suitable for the present invention may include a hydraulic, electrical, or electromechanical power unit 126 and a formation fluid extractor 128. The formation fluid extractor 128 may include an extensible suction probe 138 that is opposed by bore wall feet 140. Both, the suction probe 138 and the opposing feet 140 may be hydraulically or electro-mechanically extensible to firmly engage the well borehole wall. Construction and operational details of a suitable fluid extraction tool 128 are thoroughly described by U.S. Pat. No. 5,303,775, the specification of which is incorporated herein by reference.

A large displacement volume motor/pump unit 130 may be provided below the extractor 128 for line purging. A similar motor/pump unit 132 having a smaller displacement volume may be included in the tool in a suitable location, such as below the large volume pump, for quantitatively monitoring fluid received by the tool 120. One or more sample tank magazine sections (two are shown 134, 136) may be included for retaining fluid samples from the small volume pump 132. Each magazine section 134, 136 may have several fluid sample tanks 106.

In several embodiments to be described in further detail later, the tool 120 includes a downhole spectrometer or other evaluation tool for evaluating downhole fluids. In one embodiment, the tool 120 includes an apparatus for changing the optical behavior of a spectrometer such as a grating spectrometer using a closed loop system containing an actuator such as a micro-electromechanical systems (MEMS) actuator and a controller system. A "downhole fluid" as used herein includes any gas, liquid, flowable solid and other materials having a fluid property. A downhole fluid may be natural or man-made and may be transported downhole or may be recovered from a downhole location. Non-limiting examples of downhole fluids include downhole fluids can include drilling fluids, return fluids, formation fluids, production fluids containing one or more hydrocarbons, oils and solvents used in conjunction with downhole tools, water, brine and combinations thereof.

Figure 2:
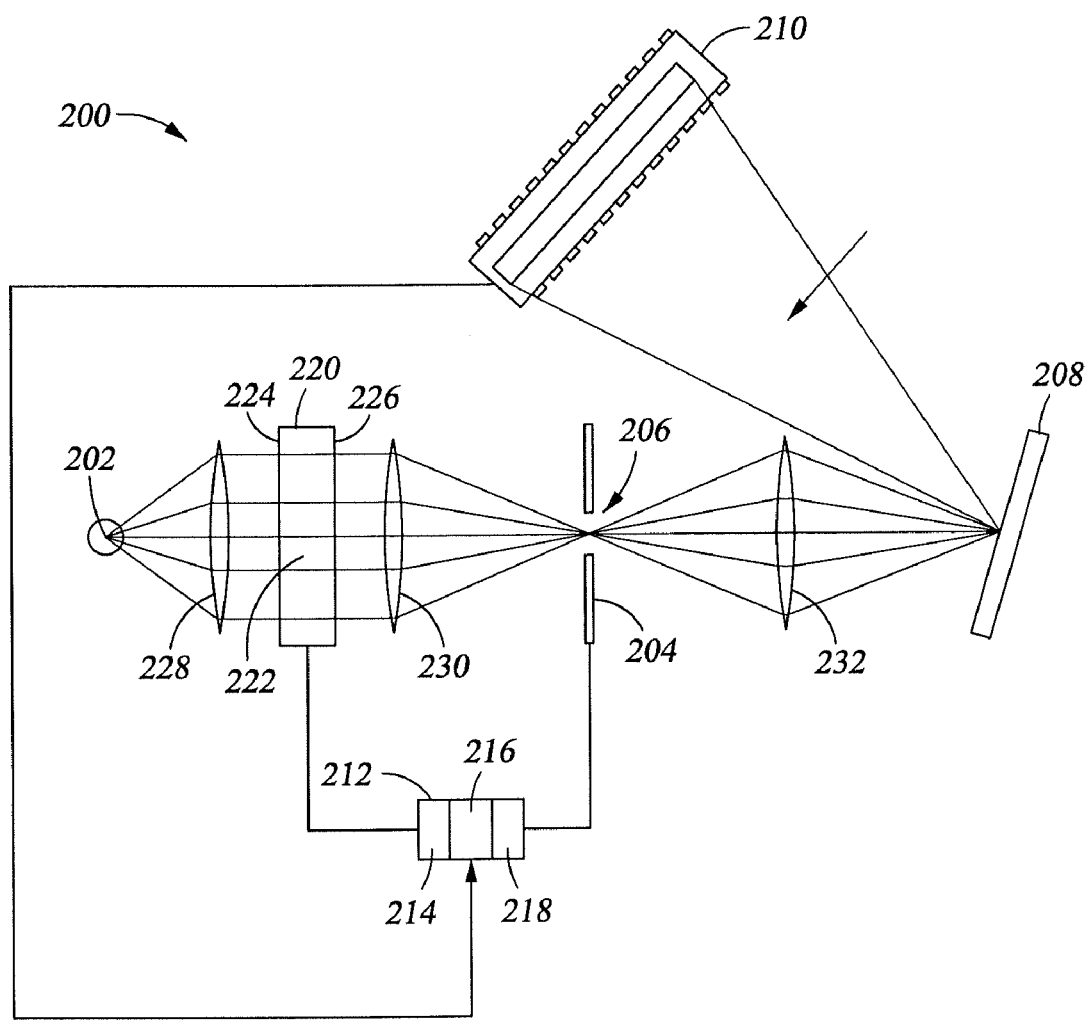
FIG. 2 illustrates a non-limiting example of a downhole spectrometer according to several embodiments of the disclosure.

FIG. 2 illustrates a non-limiting example of a downhole spectrometer 200 according to several embodiments of the disclosure that may be conveyed in a well borehole using, for example, a wireline carrier as described above and shown in FIG. 1. Those skilled in the art with the benefit of the present disclosure that any suitable carrier may be used to convey the downhole spectrometer 200 in a well borehole and will appreciate that any other suitable carrier is within the scope of the disclosure without the need for further illustration or description.

The downhole spectrometer 200 example includes an electromagnetic energy source 202 and an optical block 204 having an adjustable slit 206 or other opening that controls energy entering the spectrometer 200. A grating 208 may be disposed in an optical path leading from the optical block 204 and one or more sensors 210 may be placed in an optical path leading from the grating 208. In this example, a controller 212 may be used to adjust the slit 206 size based at least in part on one or more estimated parameters. In one or more embodiments, the controller may include a processor 214, a memory 216 and one or more programs 218 that when executed by the controller 212 or other processing device perform methods according to the disclosure.

A fluid cell 220 may be disposed between the electromagnetic energy source 202 and the optical block 204 for transmission spectroscopy. Alternatively or in addition, reflectance spectroscopy may be accomplished where electromagnetic energy is reflected and/or refracted at a fluid-probe interface. Those skilled in the art with the benefit of the present disclosure will appreciate these other embodiments are within the scope of the present disclosure without the need for further illustration or description. So for brevity, the discussion herein with respect to exemplary embodiment of FIG. 2 will remain on transmission spectroscopy.

In one or more embodiments, the fluid cell 220 may be a probe device that may be inserted into a formation or into a downhole fluid container. In one or more embodiments, the fluid cell 220 may include an internal volume 222, an input window 224 and an output window 226. The windows 224, 226 may be constructed using any material suitable for downhole use, sapphire for example. The downhole fluid in the fluid cell 220 may be stationary, flowing or may change between stationary and flowing. In one or more embodiments, the downhole fluid in the fluid cell may include single phase fluid or multi-phase fluid.

A collimating lens 228 may be used to collimate electromagnetic energy prior to interacting with the fluid cell 220. In other embodiments, the collimating lens 228 is optional depending on the electromagnetic energy output characteristics of the source 202 and/or on the optical characteristics of the fluid cell 220. In one or more embodiments, the lens 228 may be a focusing lens. A focusing lens 230 is shown in this non-limiting example placed on an opposite side of the fluid cell 220 for directing the electromagnetic energy emitted from the fluid cell 220 toward the slit 206. The lens 230 opposite the fluid cell 220 may alternatively be a collimating lens or optionally omitted depending on the particular fluid cell 220 optical characteristics. Energy passing through the slit 206 may diverge, so another lens 232 may be disposed between the optical block 204 and the grating 208 to direct electromagnetic energy 234 toward the grating 208. The lens 232 may be a focusing lens as shown in this example or may be a collimating lens depending on the particular spectrometer specifications and application.

The energy emitted from the electromagnetic energy source 202 may be modulated according to programs 218 and by the processor 212 within the same controller 212 that adjusts the slit 206 or by another controller, for example a surface controller 114 as described above and shown in FIG. 1.

In several embodiments, the electromagnetic energy source 202 may include one or more broadband light sources such as an incandescent light source along with an optical filter to provide selected wavelengths. The electromagnetic energy source 202 in some non-limiting embodiments may include one more light-emitting diodes (LED). The electromagnetic energy source 202 may also use one or more laser diodes. In other embodiments, the spectrometer 200 may include one or more electromagnetic energy sources 202 that include a combination of source types. The electromagnetic energy source 202 in several embodiments emits electromagnetic energy in a near infrared band of wavelengths, in an infrared band of wavelength or both.

The optical block 204 may be any optical block suitable for installation in a downhole tool. In one embodiment, the optical block includes components to split the light in many wavelength ranges, such as a mirror/grating combination, a fabry-perot resonator or a plurality of single line filters. Non-limiting examples of an optical block include MEMS structures, mechanical structures and combinations thereof. In one or more embodiments, a MEMS optical block 204 may be electrically coupled to the controller 212 such that control signals transmitted by the controller effect an adjustment in the slit 206 size. In one or more embodiments, the adjustment is effected by a selected voltage or charge being placed on a MEMS control electrode. In one example, the nominal range of a slit width is on the order of about 50 μm. The slit width may be adjusted in increments of, for example, 10 percent or 5 μm. In one or more embodiments, the optical block 204 may be mechanically actuated, hydraulically actuated, pneumatically actuated, and combinations thereof as will be described further below with reference to FIG. 3.

The grating 208 may be any suitable grating for a downhole spectrometer. The grating 208 may be a substantially fixed grating or the grating may be a tunable grating. One non-limiting example of a tunable grating is described in U.S. Publication US2007/0159625 A1 by DiFoggio for "Method and Apparatus for Estimating a Property of a Fluid Downhole," application Ser. No. 11/330,283, filed on Jan. 11, 2006 the entire specification of which is hereby incorporated herein by reference. The grating 208 operates on the impinging electromagnetic energy or "light" to separate the spectra of the energy and to direct the spectra to the sensor 210.

The sensor 210 may be any suitable light-sensitive sensor for receiving electromagnetic energy from the grating 208. In one or more embodiments, the sensor 210 may include a photodetector. In one or more embodiments, the sensor 210 may include a photosensitive array of sensors. In one or more embodiments, the sensor 210 may produce an output signal indicative of the received energy. The output signal may be processed by the controller 212 or by another information processor in-situ or at a surface location to estimate one or more properties of the downhole fluid in the fluid cell 220. In one or more embodiments, the output signal may be processed to estimate a signal-to-noise ratio (SNR) of the detected energy. As will be described further below, the output signal may be used at least in part to control the adjustable slit 206. The controller 212 may be programmed to autonomously control the slit width or opening size. In this mode of operation, the controller 212 receives sensor 210 output signals and the programs stored in the memory 216 may be used to estimate a corrective action. In one or more embodiments, the corrective action includes a new opening size that is transmitted by the controller to the optical block.

Figure 3:
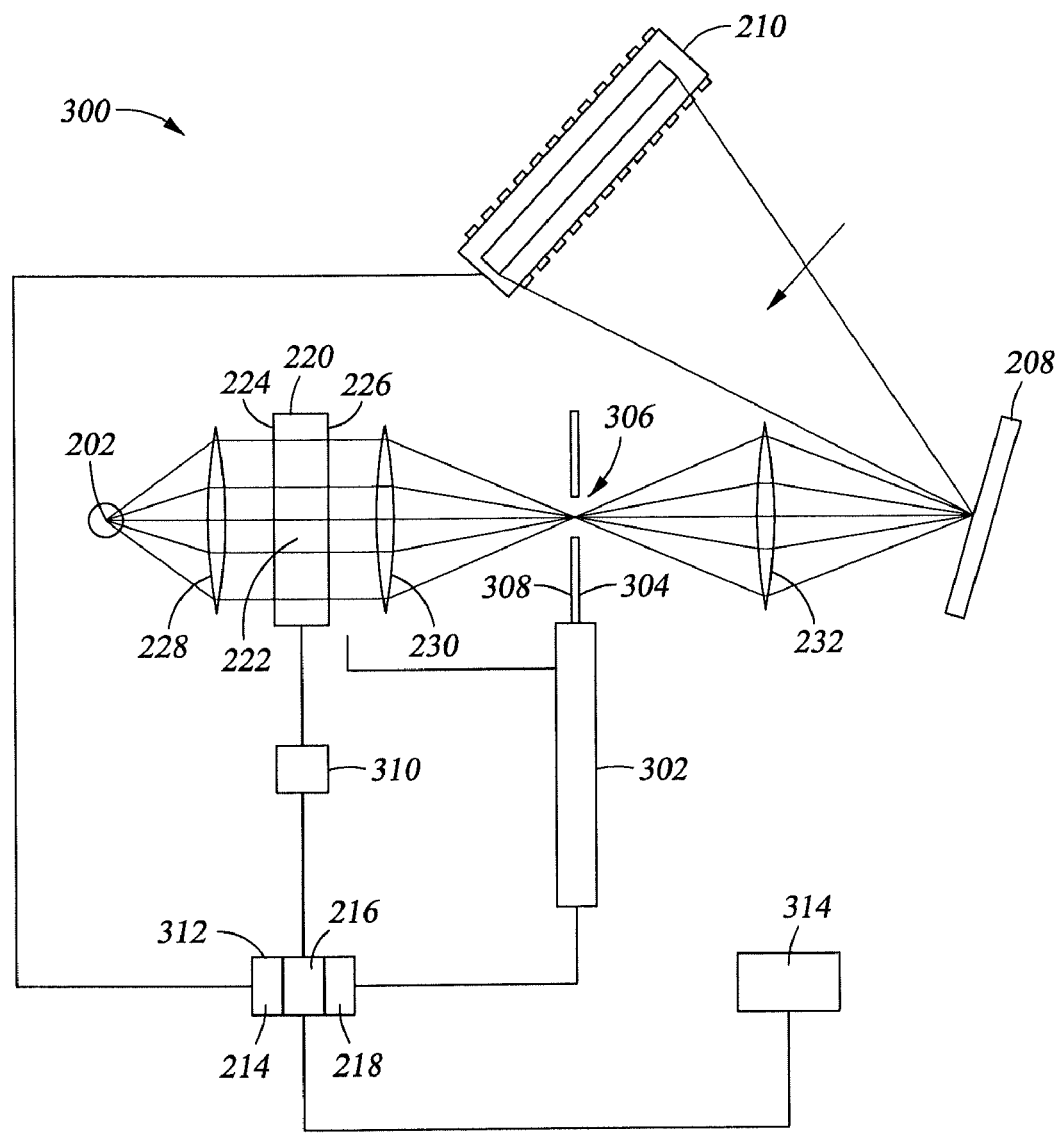
FIG. 3 illustrates another non-limiting example of a downhole spectrometer according to several embodiments of the disclosure.

Turning now to FIG. 3, a downhole spectrometer 300 may include several elements substantially as described above and shown in FIG. 2. The spectrometer 300 may include an electromagnetic energy source 202 and an optical block 304 having an adjustable opening such as a slit 306 that controls energy entering the spectrometer 300. A grating 208 may be disposed in an optical path leading from the optical block 304 and one or more sensors 210 may be placed in an optical path leading from the grating 208. In this example, a controller 312 may be used to adjust the slit 206 size based at least in part on one or more estimated parameters. The controller 312 may include a processor 214, memory 216 and programs 218 similar to the processor, memory and programs described above. The controller 312 in this non-limiting example may further receive information and estimate other parameters as will be discussed in more detail below.

A fluid cell 220 may be disposed between the electromagnetic energy source 202 and the optical block 304 for transmission spectroscopy. Alternatively or in addition, reflectance spectroscopy may be accomplished where electromagnetic energy is reflected and/or refracted at a fluid-probe interface. Those skilled in the art with the benefit of the present disclosure will appreciate these other embodiments are within the scope of the present disclosure without the need for further illustration or description. So for brevity, the discussion herein with reference to the exemplary embodiment of FIG. 3 will remain on transmission spectroscopy.

The exemplary spectrometer 300 may further include collimating and focusing lenses 228, 230, 232 as described above and shown in FIG. 2. And the energy emitted from the electromagnetic energy source 202 may be fixed or modulated as described above and may be any suitable source type as described above. In one or more embodiments, the grating 208 may be any suitable grating for a downhole spectrometer and may be fixed or tunable substantially as described above and shown in FIG. 2.

The sensor 210 may be any suitable light-sensitive sensor for receiving electromagnetic energy from the grating 208. The sensor shown in the example of FIG. 3 includes a photosensitive array that can detect the several spectra of energy from the grating 208. In one or more embodiments, the sensor 210 may include a photodiode.

FIG. 3 illustrates an exemplary embodiment that includes an actuator 302 coupled to the optical block 304 for adjusting the slit 306. In one or more embodiments, the actuator 302 may include a link 308 with the optical block 304. In one or more embodiments, the link 308 may be mechanical, electromechanical or a combination thereof. The actuator 302 in the non-limiting example of FIG. 3 includes a linear actuator such as a piezoelectric motor that is controllable via the controller 312. In one or more embodiments, the slit may include a movable edge. The edge may be moved by the actuator 302 or as in the example of FIG. 2 by varying electrical charge on a MEMS device.

One or more fluid sensors 310 may be associated with the downhole fluid under evaluation and one or more environmental sensors 314 may be associated with the downhole environment. In one or more embodiments, the fluid sensors 310 are operable to produce one or more output signals indicative of a sensed fluid parameter. In one or more embodiments, the environmental sensors 314 are operable to produce one or more output signals indicative of a sensed environmental parameter. Fluid parameters may include but are not limited to pressure, temperature, phase, flow rate, content, cleanliness and any combination thereof. Environmental parameters may include but are not limited to temperature, pressure, vibration, acceleration, position and any combination thereof. The sensors 210, 310 and 314 may be placed in communication with the controller 312 by electrical conductors, optical fibers, wireless coupling or by any other or combination of couplings to allow information transmission from the selected sensor 210, 310, 314 to the controller 312. As noted earlier, the controller 312 may be downhole, may be disposed at a surface location or may be distributed among several locations including downhole and uphole locations. The controller 312 may be programmed to autonomously control the slit 306 size. In this mode of operation, the controller 312 receives sensor output signals from the photosensitive array 210, from the fluid sensors 310, from the environmental sensors 314 or combinations of these sensors. Programs stored in the memory 216 may be used to estimate a corrective action. In one or more embodiments, the corrective action includes a new slit size that is transmitted by the controller to the optical block or to the actuator 302.

Having described the several embodiments and variations, those skilled in the art with the benefit of the present disclosure will appreciate the following operational embodiments and methods. Electromagnetic energy emitted from a source 202 passes through the collimating lens 228, when used, and through a downhole fluid sample within some volume 222 containing the downhole fluid. The energy passing through the fluid is directed to an optical block 204, 304 having an adjustable opening 206, 306 that may be in the form of a slit. The opening generates together with the diffractive element such as the grating 208, a projection of the incoming light on the sensor array 210. The wavelengths of the incoming energy are sorted from shorter to longer wavelengths by the influence of the grating 208, and the spectral resolution is a function of the opening (e.g., slit) dimension.

Figure 4:
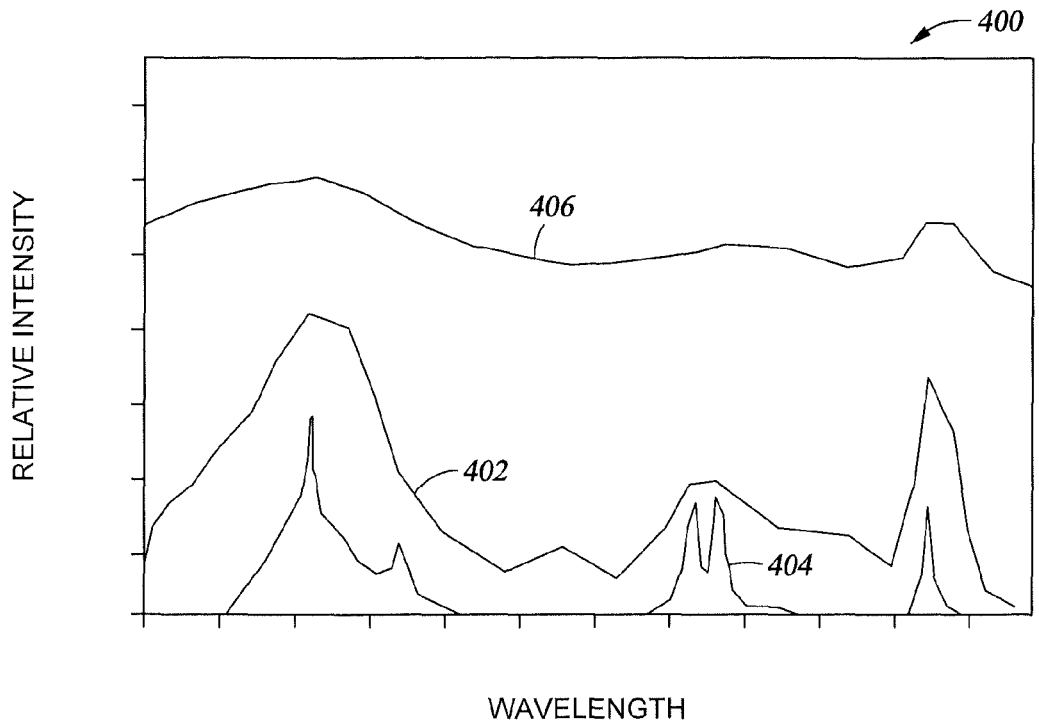
FIG. 4 shows exemplary intensity curves as a function of wavelength and slit width.

Referring now to FIG. 4, in principle a decreasing slit width causes an increasing spectral resolution. On the other hand the intensity of illumination on the sensor array 210 will be decreased by decreasing the slit width. As a result the signal-noise-ratio (SNR) will worsen, that is, there will be a lower SNR. In order to maximize the SNR, one would then measure between a higher spectral resolution at lower illumination intensity or lower spectral resolution and higher illumination intensity as shown in FIG. 2. The figure is a plot 400 to show the relationship of intensity to wavelength under varied slit dimensions. For example, the curve 402 may be considered as a reference where the slit is of a first dimension. Decreasing a slit dimension such as a slit width will result in a curve similar to the dotted curve 404. On the other hand, increasing the slit width will result in a curve having higher intensity with smoothed peaks as illustrated by the curve 406. As demonstrated herein, a narrower slit results in less light meeting the sensor, and results in sharper lines with a higher dynamic range between darkness and peaks. A broader or wider slit allows more light to pass to the sensor, with less detailed peaks and decreased dynamic rang between peaks and darkness.

Methods according to the present disclosure provide for adjusting the spectral resolution and the illumination intensity under multiple downhole conditions to optimize spectral resolution for an optimal SNR. The SNR, which will be adversely affected under the influence of an increasing downhole temperature, can be used as an indicator for a disadvantageous slit width. One advantage of the several embodiments described herein is that poor SNR may be corrected in substantially real time during fluid evaluations by changing the slit dimensions under downhole conditions, for example, based on the methane peak.

Figure 5:
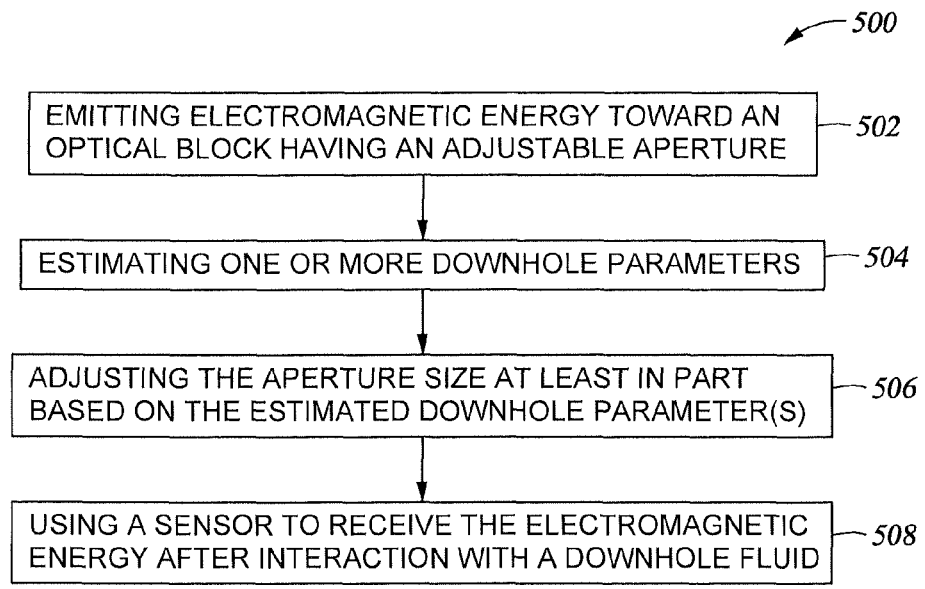
FIG. 5 is a flow of a non-limiting method example according to the disclosure.

Referring now to FIG. 5, a non-limiting method 500 for evaluating a downhole fluid includes emitting electromagnetic energy toward an optical block having an adjustable opening 502, estimating one or more downhole parameters 504, and adjusting the opening size at least in part based on the one or more estimated downhole parameters 506. The method may further include receiving with a sensor electromagnetic energy emitted by the electromagnetic energy source after the emitted electromagnetic energy interacts with a downhole fluid 508.

In one or more embodiments, the method shown in FIG. 5 may include estimating one or more downhole parameters using an output signal from the sensor 210 described above, using an output signal from one or more fluid property sensors 310, using an output signal from one or more environmental sensors 314, or by using any combination of these or other sensors. In several embodiments, the estimated parameters may include an intensity detected by the photosensitive array 210, a signal-to-noise ratio, a temperature, a fluid content or any combination thereof. In one or more embodiments, the several parameters may be estimated in substantially real time. For the purposes of the present disclosure, substantially real time includes making the estimations during the downhole fluid evaluation, prior to beginning the downhole fluid evaluation or after the evaluation and prior to a subsequent downhole fluid evaluation without tripping the tool. These substantially real-time evaluations may be used in conjunction with the controller 212, 312, 114 to provide adjusting the opening size under substantially autonomous control by the controller. In some embodiments, adjusting the opening size may be accomplished using a piezoelectric motor, a mechanical actuator, an electro-mechanical actuator or a combination thereof. These devices may be coupled to or otherwise in communication with the controller as described above.

A method according to one or more embodiments may include emitting electromagnetic energy using a broadband source, a narrow band source, a laser diode, an LED or combinations thereof. Emitting electromagnetic energy may also include using a near infrared light source. In one embodiment, the light source is a broadband source used in conjunction with liquids or other materials to be investigated, which absorb different "lines" from the energy in different spectral ranges.

So the light source must cover all interesting wave length ranges without brakes. A LED or a Laser diode has a sharp bordered wavelength, so that a narrow band source doesn't make sense.

Where a grating 208 is used, a method may include receiving electromagnetic energy from the adjustable opening with the grating and separating the received electromagnetic energy into a plurality of spectra using the grating. The grating 208 may be adjustable or tunable as described above.

The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein, use of equivalent functional couplings for couplings described herein, and/or use of equivalent functional actions for actions described herein. Such insubstantial variations are to be considered within the scope of the claims below.

What is claimed is:

1. An apparatus for evaluating downhole fluids comprising:
an environmental sensor configured to estimate one or more downhole environmental parameters in a borehole environment;
an optical block having an adjustable opening that receives electromagnetic energy emitted by an electromagnetic energy source;
a controller operatively associated with the optical block for adjusting the opening size, wherein the opening size is adjusted based on a signal from the environmental sensor, the signal indicative of the one or more estimated downhole environmental parameters; and
an electromagnetic energy sensor that receives the electromagnetic energy emitted by the electromagnetic energy source after the emitted electromagnetic energy interacts with a downhole fluid.

2. An apparatus according to claim 1, wherein the opening is a slit, and the opening size is a slit width.

3. An apparatus according to claim 1, wherein the controller is configured to estimate the one or more environmental parameters and adjust the opening size based on a signal-to-noise ratio associated with the one or more environmental parameters.

4. An apparatus according to claim 1, wherein the estimated downhole environmental parameter includes a temperature.

5. An apparatus according to claim 1, wherein the estimated downhole environmental parameter includes pressure, temperature, phase, flow rate, content, cleanliness, vibration, acceleration, position and any combination thereof.

6. An apparatus according to claim 1, wherein the controller is disposed at a surface location, at a downhole location, or is distributed among a plurality of locations.

7. An apparatus according to claim 1, wherein estimated parameters include substantially real-time estimated parameters.

8. An apparatus according to claim 1, wherein the controller provides substantially autonomous control of the opening size adjustment.

9. An apparatus according to claim 1, wherein the optical block includes a MEMS structure, the adjustable opening being adjustable by controlling the MEMS structure.

10. An apparatus according to claim 1, further comprising an actuator operably associated with the optical block and the controller, wherein the actuator adjusts the opening size in response to a signal from the controller.

11. An apparatus according to claim 10, wherein the actuator includes a piezoelectric motor, a mechanical actuator, an electro-mechanical actuator or a combination thereof.

12. An apparatus according to claim 1, wherein the electromagnetic energy source includes one of a broadband source, a narrow band source, a laser diode, and an LED.

13. An apparatus according to claim 1, wherein the electromagnetic energy source includes a near infrared light source.

14. An apparatus according to claim 1, wherein the electromagnetic energy sensor includes one or more of a photodetector and a photosensitive array.

15. An apparatus according to claim 1, wherein the environmental sensor includes a fluid sensor.

16. An apparatus according to claim 1, further comprising a grating receiving electromagnetic energy from the adjustable opening, the grating being operable to separate the received electromagnetic energy into a plurality of spectra.

17. An apparatus according to claim 16, wherein the grating comprises a tunable grating.

18. A method for evaluating downhole fluids comprising:
emitting electromagnetic energy toward an optical block having an adjustable opening;
estimating one or more downhole environmental parameters via an environmental sensor disposed in a borehole environment;
adjusting the opening size based on a signal from the environmental sensor, the signal indicative of the one or more estimated downhole environmental parameters using a controller; and
receiving, with an electromagnetic energy sensor, electromagnetic energy emitted by the electromagnetic energy source after the emitted electromagnetic energy interacts with a downhole fluid.

19. A method according to claim 18, wherein estimating one or more downhole environmental parameters includes using an output signal from the electromagnetic energy sensor, using an output signal from one or more fluid property sensors, or any combination thereof.

20. A method according to claim 18, wherein the estimating one or more downhole environmental parameters includes estimating an intensity detected by the sensor, includes estimating a signal-to-noise ratio, estimating a temperature, estimating a fluid content or any combination thereof.

21. A method according to claim 18, wherein estimating the one or more parameters includes estimating the parameters in substantially real-time.

22. A method according to claim 18, wherein adjusting the opening size comprises substantially autonomous control by the controller.

23. A method according to claim 18, wherein adjusting the opening size includes using a piezoelectric motor, a mechanical actuator, an electro-mechanical actuator or a combination thereof.

24. A method according to claim 18, wherein emitting electromagnetic energy includes using a broadband source, a near infrared light source, a narrow band source, a laser diode, an LED or combinations thereof.

25. A method according to claim 18, wherein adjusting includes adjusting the opening size based on a signal-to-noise ratio associated with the one or more environmental parameters.

26. A method according to claim 18, further comprising receiving electromagnetic energy from the adjustable opening with a grating and separating the received electromagnetic energy into a plurality of spectra.

27. A method according to claim 26, wherein the grating comprises a tunable grating.

28. An apparatus according to claim 1, wherein the controller is configured to automatically adjust the opening size in response to the signal from the environmental sensor.

29. A method according to claim 18, wherein the opening size is automatically adjusted in response to the signal received by the controller from the environmental sensor.

* * * * *